(12) United States Patent
Hall

(10) Patent No.: US 8,966,696 B2
(45) Date of Patent: Mar. 3, 2015

(54) TOOTHBRUSH WITH AUTOMATIC ACTUATION

(75) Inventor: Scott E. Hall, Issaquah, WA (US)

(73) Assignee: Koninklijke Philips N.V., Eindhoven (NL)

( * ) Notice: Subject to any disclaimer, the term of this patent is extended or adjusted under 35 U.S.C. 154(b) by 111 days.

(21) Appl. No.: 13/513,701

(22) PCT Filed: Nov. 22, 2010

(86) PCT No.: PCT/IB2010/055349
§ 371 (c)(1),
(2), (4) Date: Jun. 4, 2012

(87) PCT Pub. No.: WO2011/077290
PCT Pub. Date: Jun. 30, 2011

(65) Prior Publication Data
US 2012/0246846 A1 Oct. 4, 2012

Related U.S. Application Data

(60) Provisional application No. 61/289,652, filed on Dec. 23, 2009.

(51) Int. Cl.
*A61C 17/34* (2006.01)
*A61C 17/22* (2006.01)
*A46B 15/00* (2006.01)

(52) U.S. Cl.
CPC ............ *A61C 17/221* (2013.01); *A46B 15/0004* (2013.01)
USPC .............................................. 15/22.1; 433/32

(58) Field of Classification Search
USPC .............................................. 15/22.1; 433/32
See application file for complete search history.

(56) References Cited

U.S. PATENT DOCUMENTS

| 2003/0135940 | A1 | 7/2003 | Lev et al. |
| 2005/0011025 | A1 | 1/2005 | Hilscher et al. |
| 2005/0050658 | A1 * | 3/2005 | Chan et al. ............... 15/22.1 |
| 2006/0279896 | A1 | 12/2006 | Bruwer |
| 2009/0087813 | A1 | 4/2009 | Cai et al. |

FOREIGN PATENT DOCUMENTS

| EP | 1980375 A1 | 10/2008 |
| GB | 2030855 A | 4/1980 |
| JP | 8275961 A | 10/1996 |

* cited by examiner

*Primary Examiner* — Randall Chin

(57) ABSTRACT

The power toothbrush includes a handle (12) and a brushhead (18) having a conductive electrode sensing element (25) therein. The toothbrush includes a driver assembly (14) for the brushhead and a sensor system (28) for measuring the capacitance between the sensing element on/in the brushhead and an electronics ground (27) in the handle of the toothbrush. A microprocessor/controller (26) is programmed to determine whether the measured capacitance is above a threshold value, which indicates that the toothbrush is near or within the mouth of the user. The microprocessor actuates the driver assembly for operation of the toothbrush when the capacitance value is above the threshold value.

15 Claims, 2 Drawing Sheets

TOOTHBRUSH WITH AUTOMATIC ACTUATION

This invention relates generally to power toothbrushes, and more specifically concerns the actuation of a power toothbrush.

Typically, a power toothbrush includes a mechanical, i.e. tactile, switch to turn it on and off. For some users, particularly disabled users, a mechanical switch is difficult to operate. It would thus be advantageous to be able to actuate a power toothbrush without having to operate a mechanical switch. One known system for actuating a power toothbrush without a switch includes the use of conductive electrodes on the outer surface of the toothbrush to complete an electrical circuit between the electrode surfaces and the user's saliva or the gum tissue. However, such a system can produce an unpleasant taste or sensation in the mouth due to the electrical contact made by the conductive members on the toothbrush. The system also can be expensive, complex in operation and unreliable over many uses.

Effective, reliable automatic actuation of a toothbrush also has the advantage of being useful in some systems to ensure that only authorized brushheads are used in the toothbrush. The use of unauthorized brushheads remains a significant problem.

Accordingly, the automatically actuated power toothbrush comprises: a handle; a brushhead which includes a set of bristles; a driver assembly for the brushhead; a conductive electrode in or on the brushhead; a system for measuring the capacitance between the conductive electrode and a toothbrush ground in the handle; and a controller programmed to determine whether the measured capacitance is above a pre-established threshold value, indicative that the toothbrush is near or within the mouth of the user, and thereafter for actuating the driver assembly for operation of the toothbrush.

Also, the brushhead for use in a power toothbrush, wherein the toothbrush includes a driver assembly for the brushhead assembly and a system for measuring the capacitance between a conductive electrode on the brushhead assembly and an electronics ground in a handle portion of the toothbrush, the brushhead, comprises: a brushhead which is insertable onto and removable from the remainder of the power toothbrush, the brushhead itself having a value of capacitance which is part of a total capacitance between the conductive electrode and the electronics ground which is above such a pre-selected threshold value or within such a pre-selected range for actuation of the toothbrush, indicative that the brushhead is an authorized brushhead for the toothbrush.

In general, the toothbrush disclosed herein includes a system for automatic actuation, i.e. automatic turn on and turn off, of the toothbrush. In particular, it uses the change in circuit capacitance between a sensor element on the toothbrush brushhead near the bristles and an electronic (circuit) ground point on the toothbrush handle when the toothbrush is in or near the mouth to actuate the toothbrush. When a power toothbrush is positioned by a user in or near their mouth, the capacitance between a sensing element on or within a toothbrush brushhead and the electronics ground on the toothbrush changes significantly, due to the proximity of the sensing element to the large conductive surfaces in the mouth. The change in capacitance from the nominal capacitance between the sensing element and the toothbrush electronics ground when the toothbrush is outside of the mouth can be readily measured and used to actuate the toothbrush. The change in capacitance occurs as a result of the effect that the conductive tissues of the mouth have on the static electric field in the vicinity of the brushhead, even without actual physical contact between the brushhead and the gums, saliva or teeth of the user.

Figure 1:
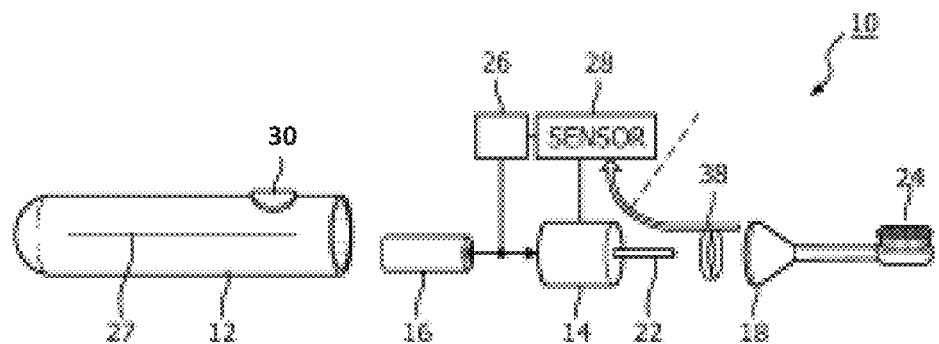
FIG. 1 is an exploded view of the toothbrush described herein.
Figure 2:
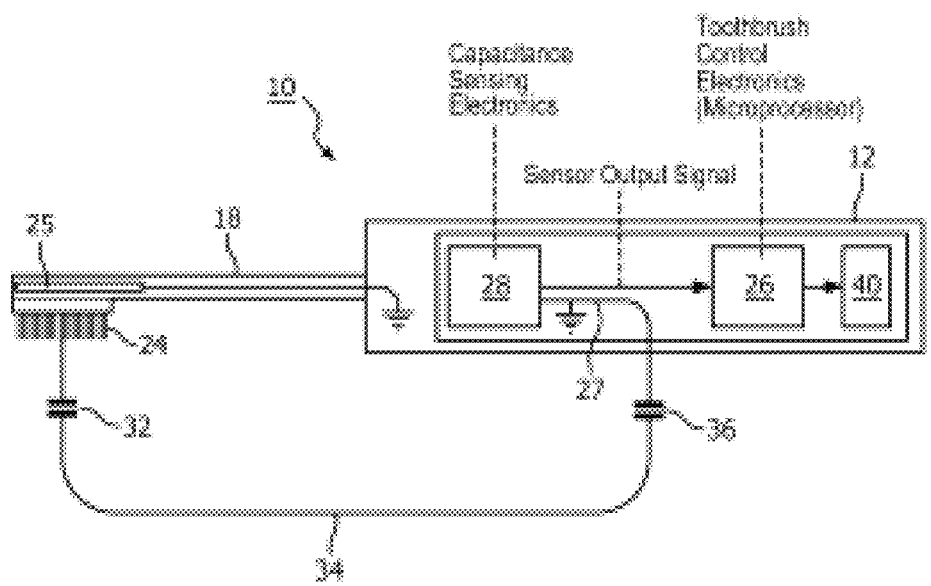
FIG. 2 is a diagram illustrating the measurement of capacitance.

Referring now to FIGS. 1 and 2, where FIG. 1 illustrates the toothbrush and FIG. 2 is more illustrative of the capacitance measuring function, toothbrush 10 includes a handle portion 12 and a DC motor 14 which is powered by a battery 16, the motor providing the driving action for a brushhead 18, which in turn is removably mounted on a motor driveshaft 22. It should be understood, however, that various driving action arrangements can be used in a power toothbrush which incorporates the present automatic actuation system. The illustration of a DC motor is only one of several possible motor systems.

Brushhead 18 includes a set of bristles 24 mounted on a bristle back member 25 which defines the bristle portion of the brushhead, the bristles 24 accomplishing cleaning through an oscillatory action provided by motor 14. The operation of motor 14 is controlled by a microprocessor/controller 26 which is a common component of power toothbrushes. Toothbrush 10 includes a capacitance sensor system 28 which measures the capacitance between a conductive electrode/sensing element 25 on or in the brushhead 18, typically positioned close to the bristles 24, and the electronics ground plane represented at 27 in handle 12 in FIG. 1. Such a capacitance sensor system 28 is conventional and commercially available from a variety of manufacturers.

Figure 3:
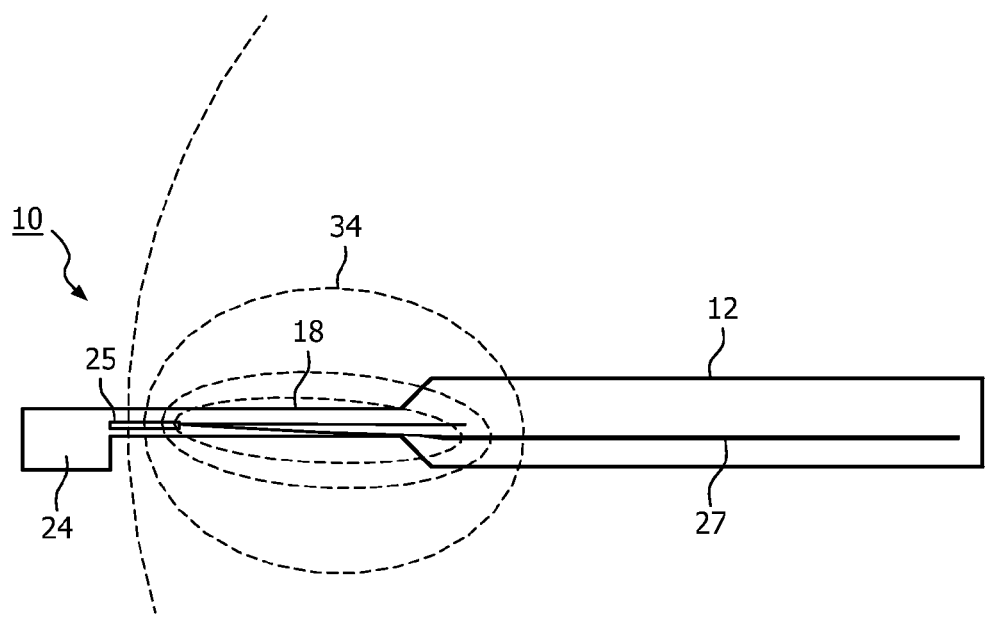
FIG. 3 is a diagram illustrating electric field coupling between a sensor element on the brushhead and a toothbrush ground when the toothbrush is outside the mouth.

The conductive electrode/sensing element 25 is shown in the form of a pin 25 in the brushhead of FIG. 2. The metal pin 25 is positioned near bristle set 24. Other electrode/sensing element arrangements could be used, including a metal coating or wrapper. Of most importance to the present system relative to the position of the electrode element on the brushhead is that the pattern of static electric field lines between the conductive electrode and the toothbrush electronics ground plane in the handle is significantly altered when the electrode is brought near to or into the mouth. Referring to FIG. 3, when the toothbrush head is distant from the mouth of a user, the capacitance measured by sensor system 28 results from the fringe field represented by field lines 34 of the approximate electric field between conductive electrode 25 and the electronics ground plane 27 in handle 12. Since the conductive electrode and the ground plane are separated by a comparatively large distance, the electric field coupling is weak and the resulting capacitance is small, less than a picofarad.

Figure 4:
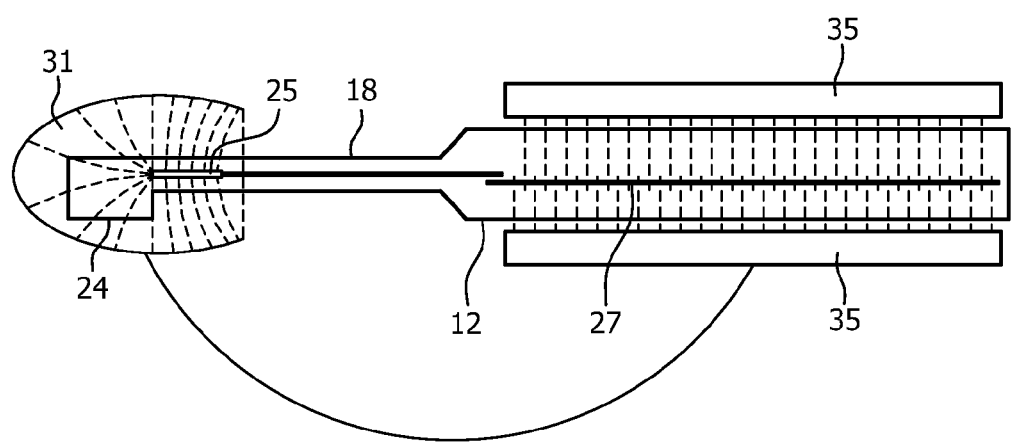
FIG. 4 is a diagram illustrating electric field coupling when the toothbrush is inside the mouth.

Referring to FIG. 4, when the brushhead is brought near or into the mouth, represented at 31, the capacitance between electrode 25 and electronics ground 27 is strongly influenced by the tissues of the mouth, the capacitance of which is represented at 32 in FIG. 2 and the capacitance between the electronics plane and the user's gripping hand 35 in FIG. 4, represented at 36 in FIG. 2. FIG. 4 illustrates the human body electrically modeled as a single large conductive member. The proximity of the toothbrush brushhead to the mouth and the gripping of the fingers 35 of the user around the handle 12 provides much tighter coupling of the electric field lines from the conductive electrode to the electronics ground in the handle. The mouth of the user and the conductive path to the user's hand provides a short circuit for the conductive field.

Typically, the coupling of FIG. 4 when the toothbrush is inside the mouth increases the total capacitance by a factor of 1000 compared to the coupling shown in FIG. 3 when the toothbrush is outside of the mouth.

The measured capacitance value from sensing circuit 28 is provided to microprocessor 26, which is programmed to determine whether or not the measured capacitance value is greater than a set threshold value. The threshold value is pre-established to be approximately the value of capacitance when the toothbrush is held inside the mouth. If the determined capacitance value is less than the threshold value, the toothbrush remains in an off condition. However, if the determined capacitance is greater than the threshold value, the microprocessor transmits an electronic signal to a switch 40 in the handle 12 (FIG. 2) to initiate operation of the drive system (motor) 14. The toothbrush will then operate for a selected time, determined by the microprocessor, or will turn off if the toothbrush is removed from the mouth. In one embodiment, the toothbrush will operate at a frequency near to or at the resonate frequency of the toothbrush, although such operation is not necessary to use of the capacitance based actuation system described herein.

The toothbrush can also incorporate a tactile switch 30 (FIG. 1), such that the toothbrush will only operate when both switch 30 is operated and the determined capacitance is above the threshold value.

The capacitance actuation system described above, besides having the advantage of producing an automatic actuation of the toothbrush when positioned in or near the mouth of the user, thereby potentially eliminating the need for a mechanical switch, can also be used to ensure that only authorized brushheads can be used with the handle 12 of the toothbrush. If a brushhead is inserted onto the handle of the toothbrush, and the resulting measured capacitance by sensor 28 to electronics ground is not above the pre-established threshold value, or within a unique pre-selected range of capacitance, then the toothbrush will not be actuated. This result requires that the capacitance of the brushhead itself be sufficiently different from otherwise available brushheads to produce a range of capacitance exclusivity for the authorized brushheads, meaning that only authorized brushheads produce a capacitance value which is above the selected capacitance threshold or within a specific range of capacitance recognized by the microprocessor as characteristic of an authorized brushhead assembly. A capacitance enhancement element may be added to the brushhead during manufacture to insure this exclusivity, i.e. the range of capacitance accepted by the toothbrush system includes the capacitance of the new brushhead, but excludes a capacitance value produced by previously commercially available brushheads.

This capacitance enhancement element can take various forms. However, in the embodiment shown it is a metal ring 38 (FIG. 1) which is positioned in the brushhead near a proximal end 40, encircling the motor drive shaft when the brushhead is inserted onto the drive shaft. Again, in such an arrangement, previously available brushheads, which otherwise would operate when positioned on the toothbrush, will not operate, since they do not have the appropriate capacitance value to produce the total capacitance required for actuation of the toothbrush. Other enhancement members can be used, including a metal pin or tube, for example, can be used.

This embodiment with the capacitance element can also be used in combination with a mechanical switch if desired to produce actuation of the toothbrush.

Hence, a toothbrush has been disclosed which is automatically actuated by a capacitance-based sensor, determining the capacitance between a conductive electrode on the brushhead and an electronics ground plane or point when the toothbrush is positioned near or in the mouth of the user. Such a system can also be used to ensure that only authorized replacement brushheads can be used with the toothbrush.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A power toothbrush, comprising:
   a handle;
   an electric ground associated with the handle;
   a brushhead which includes a set of bristles;
   a driver assembly for the brushhead;
   a conductive electrode in or on the brushhead;
   the conductive electrode and the electric ground being operatively sized and positioned within the toothbrush to capacitively store an electric charge;
   a system for measuring the capacitance between the conductive electrode and the toothbrush ground in the handle; and
   a controller programmed to determine whether the measured capacitance is above a pre-established threshold value, indicative that the toothbrush is near or within the mouth of the user, and thereafter for actuating the driver assembly for operation of the toothbrush.

2. The power toothbrush of claim 1, wherein the conductive electrode is a pin embedded in the brushhead adjacent the set of bristles.

3. The power toothbrush of claim 1, including an on/off switch operable by the user wherein the driver assembly is actuated when the on/off switch is on and the measured capacitance is above the pre-selected threshold value.

4. The power toothbrush of claim 1, wherein the toothbrush operates at a frequency which is at or near the resonant frequency of the toothbrush.

5. The power toothbrush of claim 1, wherein the brushhead is removable from the handle, and wherein the brushhead includes an additional capacitance element which permits determination of authorized brushheads.

6. The power toothbrush of claim 5, wherein the additional capacitance element is a metal ring, positioned in the vicinity of the proximal end of the brushhead.

7. The power toothbrush of claim 5, wherein the capacitance element is a selected one of a metal pin, metal tube or metal coating.

8. A brushhead for use in a power toothbrush, wherein the toothbrush includes a driver assembly for the brushhead and a system for measuring the capacitance between a conductive electrode on the brushhead and an electronics ground in a handle portion of the toothbrush, the brushhead comprising:
   a brushhead which is insertable onto and removable from the remainder of the power toothbrush, the brushhead itself having a value of capacitance which is part of a total capacitance between the conductive electrode and the electronics ground which is above such a pre-selected threshold value or within such a pre-selected range for actuation of the toothbrush, indicative that the brushhead is an authorized brushhead for the toothbrush.

9. The brushhead of claim 8, wherein the toothbrush is not actuated unless a mechanical user-operated switch is operated, in addition to the capacitance being above the threshold level or within the pre-selected range.

10. The brushhead of claim 8, wherein the selected value of capacitance includes a supplemental capacitance member in the brushhead.

11. The brushhead of claim 10, wherein the supplemental capacitance member is a metal ring.

12. The brushhead of claim 11, wherein the metal ring is positioned in the vicinity of a proximal end of the brushhead.

13. The brushhead of claim 10, wherein the supplemental capacitance member is a metal pin, metal tube or metal coating.

14. In a power toothbrush which includes:
a handle;
a brushhead which includes a set of bristles; and
a driver assembly for the brushhead,
the improvement comprising:
   a conductive electrode in or on the brushhead;
   an electric ground associated with the handle;
   the conductive electrode and the electric ground being operatively sized and
   positioned within the toothbrush to capacitively store an electric charge;
   a system for measuring the capacitance between the conductive electrode and the toothbrush ground in the handle; and
   a controller programmed to determine whether the measured capacitance is above a pre-established threshold value, indicative that the toothbrush is near or within the mouth of the user, and thereafter for actuating the driver assembly for operation of the toothbrush.

15. In the power toothbrush of claim 14, the improvement wherein the conductive electrode is a pin embedded in the brushhead adjacent the set of bristles.

\* \* \* \* \*